United States Patent [19]

Eisentraut

[11] 4,066,410

[45] Jan. 3, 1978

[54] THYROID HORMONE ASSAY

[75] Inventor: Anna M. Eisentraut, Dallas, Tex.

[73] Assignee: Nuclear-Medical Laboratories, Inc., Dallas, Tex.

[21] Appl. No.: 654,541

[22] Filed: Feb. 2, 1976

Related U.S. Application Data

[63] Continuation-in-part of Ser. No. 613,092, Sept. 15, 1975, abandoned.

[51] Int. Cl.² ............................................. G01N 33/16
[52] U.S. Cl. .................................. 23/230.6; 23/230 B; 424/1
[58] Field of Search ................ 23/230 B, 230.3, 230.6; 424/1, 1.5

[56] References Cited

U.S. PATENT DOCUMENTS

| | | | |
|---|---|---|---|
| 3,776,698 | 12/1973 | Eisentraut | 23/230 B |
| 3,850,577 | 11/1974 | Ashkar | 23/230 B |
| 3,872,225 | 3/1975 | Coller et al. | 424/1 |
| 3,911,096 | 10/1975 | Chopra | 424/1 |

OTHER PUBLICATIONS

Rubenstein et al., *J. Clin. Endo. and Metab.*, vol. 37, pp. 247–253 (1973).
Unger et al., *J. Clin. Invest.*, vol. 42, pp. 1031–1039 (1963).
Ratcliffe, *Br. Med. Bull.*, vol. 30, pp. 32–37 (1974).
Burke et al., *Br. Med. Bull.*, vol. 30, pp. 93–99 (1974).

*Primary Examiner*—Robert M. Reese
*Attorney, Agent, or Firm*—Richards, Harris & Medlock

[57] ABSTRACT

A "single tube" thyroid hormone assay is provided whereby endogenous thyroid hormone is initially separated from a serum sample with an acid reagent and thereafter a tracer amount of radioactive labelled thyroid hormone is allowed to competitively bind with antibodies for thyroid hormone. The resulting free hormone (not bound to antibody) is separated from the hormone bound to such antibodies by contacting the solution with an aqueous solution of water-soluble sulfate salt containing a minor but effective amount of added animal serum to cause precipitation of the hormone bound to the thyroid hormone binding protein material. Thereafter, either the free hormone in supernatant fluid or the bound hormone that has precipitated is counted with a scintillation counter.

20 Claims, No Drawings

THYROID HORMONE ASSAY

BACKGROUND OF THE INVENTION

This is a Continuation-in-Part of copending U.S. patent application Ser. No. 613,092, filed Sept. 15, 1975, now abandoned. This invention relates to diagnostic tests for determining the level of thyroid hormone within a body fluid. In another aspect, this invention relates to an improved test for measuring total thyroid hormone in a sample of serum. In another aspect, this invention relates to a novel radioimmunoassay for thyroid hormone.

Various diagnostic tests are known for determining thyroid function. These tests include the basal metabolism test, the thyroid uptake test, various colorimetric and chemical procedures for determining the level of thyroxine iodine in the blood and a test commonly referred to as the T-3 uptake test which measures the unsaturated binding capacity of thyrobinding globulin and other thyroxine binding proteins within a serum sample. Perhaps the most commonly used test available is the diagnostic test which utilizes radioisotopically labelled hormone to determine the level of thyroid hormone thyroxine ($C_{15}H_{11}I_4NO_4$) present in serum. This test, commonly referred to as T-4 assay, measures the total quantity of hormone within a sample of blood serum. The most commonly used T-4 assay which determines the level of thyroxine within a sample of blood serum, utilizes the technique of competitive protein binding. To carry out the T-4 assay, it is necessary first to release the thyroid hormone thyroxine from endogenous thyroxine binding proteins present in a serum sample. After this, a known quantity of thyroxine binding protein (generally thyroid hormone binding globulin) and a tracer quantity of radioactively labelled thyroid hormone are added to the thyroxine obtained from the sample. The thyroxine including the endogenous thyroxine obtained from the sample and the radioactively labelled thyroxine compete for binding sites on the known quantity of thyroxine binding protein. After the competitive binding step, the free or unbound thyroxine is separated from the thyroxine bound to the thyroxine binding proteins and the relative quantity of thyroxine in the original sample is determined by counting the radioactivity of either the free thyroxine or the bound thyroxine in a scintillation well counter.

Recently the competitive protein binding assays for thyroid hormone have been modified to include the use of specific antibodies as the thyroxine binding protein instead of the thyroxine binding globulins. Such procedures are called radioimmunoassays of thyroid hormone.

In general, the methodology of the T-4 competitive protein binding assay and the radioimmunoassay is quite similar. In both procedures, it is necessary first to release thyroxine from endogenous thyroxine binding proteins present in the serum and to alter the thyroxine binding proteins in such a way that their further participation in the reaction is prohibited. In the conventional T-4 competitive protein binding assays, this has been accomplished by initially treating the serum sample with organic solvents such as ethyl alcohol to denature the thyroid hormone binding protein. Such a procedure is described in U.S. Pat. No. 3,666,854. Other chemical methods have been utilized which include the treatment of the sample with inorganic chemicals such as alkaline solutions. However, the use of alkaline extraction solutions as commercial test kit components is not desirable because such solutions exhibit instability during storage and use. More specifically, such solutions rapidly absorb $CO_2$ which results in a lowering of the pH thereof. Another method includes the treatment of the sample with an acid solution to effect separation between the thyroid hormone and the thyroid hormone binding protein and thereafter contacting the solution with an inorganic crystalline sorbent such as magnesium silicate which sorbs the free hormone only. Such a method is described in U.S. Pat. No. 3,776,698. Generally, when acid extractions have been utilized in competitive protein binding assays, the precipitated endogenous proteins are physically removed from the resulting endogenous thyroid hormone prior to proceeding with subsequent steps in the test procedure which occur at higher pH's. This is due mainly to the fact that acid precipitated or denatured proteins are known to be resolubilized or renatured in solutions of higher pH. Thus acid denaturation is believed to be "reversible". Indeed a commercially available so-called normalized T-4 type test sold under the trademark of "Quantisorb-125" by Abbott Laboratories utilizes this above described phenomenon of renaturation of acid denatured proteins as an essential step thereof.

Another approach for releasing the thyroxine from the endogenous thyroxine binding protein is by heat denaturation. Heat denaturation of the serum protein provides good recovery of the thyroid hormone with extraction efficiencies approaching about 100%. However, this method is time-consuming in that it requires a minimum of 15 minutes in a boiling water bath for complete destruction of binding proteins.

Likewise, when carrying out the radioimmunoassay for thyroxine, it is first necessary to release the thyroxine from endogenous thyroxine binding proteins present within the serum sample and to alter the thyroxine binding proteins in such a way that their further participation in the reaction is prohibited. In the radioimmunoassay, this is most commonly accomplished to a degree by blocking the thyroxine binding sites on endogenous proteins with chemicals such as 8-anilino-1-naphthalene sulfonic acid, diphenylhydantoin, salicylates, or thimerosal. However, the use of such blocking agents in radioimmunoassay has posed problems. For example, it has been shown that the quantity of these blocking agents necessary to occupy all sites may be related to the level of endogenous thyrobinding protein which can vary significantly in individual serum samples.

Thus, in both the conventional T-4 competitive protein binding assay and the radioimmunoassay, the thyroxine must initially be extracted from native proteins and thereafter bound to specific proteins, and then the free hormone separated from the protein bound hormone. The final separation has been accomplished by sorption of the free hormone such as to resins, charcoal or inorganic crystalline sorbents. The conventional resins include ion exchange resins such as the ion exchanger having strongly basic amino or quaternary ammonium groups such as disclosed in U.S. Pat. No. 3,414,383. These organic ion exchange resins can be either in loose form or incorporated in polyurethyane sponges as disclosed in U.S. Pat. No. 3,206,602, or enclosed in porous bags or the like. Other conventional methods include a selective sorption of the free hormone by charcoal which has been coated with suitable proteins or other polymers, or the use of molecular sieves such as Sephadex. The use of the inorganic crystalline sorbent materials are disclosed in U.S. Pat. No. 3,666,854 and U.S. Pat. No. 3,776,698. In general, the methods which rely on sorption systems to separate the free hormone from the hormone bound to the protein are dependent upon protein concentration in the assay system, and some systems may require adjustment of the protein level for valid results. In addition, some of the sorbents such as the resins are temperature sensitive necessitating correction of assay values obtained in working conditions where the temperatures are variable. In addition, the sorbents are in general time dependent and careful timing during the sorption process is necessary in order to obtain reproducible results.

Antibody-bound hormone may be separated from the free fraction by precipitation of the specific protein. One common approach used to precipitate the bound fraction is the double antibody technique which, due to a second incubation period, is time-consuming. Another means of separation is chemical precipitation of the bound fraction with either high molecular weight polymers or salts. In order to precipitate the minute amounts of gamma globulin present, exogenous gamma globulin is conventionally added to the assay system prior to separation of the bound and free fractions.

A problem which has been encountered is the phenomenon of non-specific binding occurring during the assay. Non-specific binding stated simply is the binding of the free hormone including the free radioactively labelled hormone with materials other than the thyrobinding protein in the conventional T-4 assay or the antibody in the radioimmunoassay. The inability to assess the degree of non-specific binding occurring in the absence of the binding protein is a disadvantage of those assay systems in which binding protein and radioactively labelled hormone are employed as a single reagent.

In general, a thyroid hormone assay is needed which will initially extract all or substantially all of the thyroid hormone from the endogenous serum sample in a reproducible manner, will not rely on blocking agents or solid sorbents to separate the bound from the free hormone after the competitive binding step, but will effect the separations quickly and efficiently in a reporducible manner wherein a low but reproducible amount of non-specific binding will occur during each test and which can be carried out in a single test tube without the requirement of intermediate decanting of test solution(s) therefrom.

SHORT STATEMENT OF THE INVENTION

In accordance with one embodiment of the subject invention, a radioimmunoassay for thyroid hormone is provided which includes the initial extraction of endogenous thyroid hormone from sample serum with an acid reagent to result in an effective inactivation of endogenous thyroid hormone binding proteins, the subsequent adjustment of the pH to a high level suitable for competitive binding (without removing the endogenous thyroid hormone binding protein therefrom) and the addition of a tracer quantity of radioactively labelled thyroid hormone and a known quantity of thyroid hormone antibodies and thereafter allowing the resulting solution to equilibrate and competitive binding to occur, and then separation of the bound moiety from the free moiety by the addition of an aqueous sulfate salt solution which causes precipitation of the bound moiety; and thereafter counting the precipitated bound moiety or the supernatant containing the free moiety in a scintillation well counter. This procedure is carried out in a single tube without intermediate decanting steps.

In accordance with another embodiment of the subject invention, I have found that the separation of free from bound thyroid hormone fractions which results from the competitive binding step in a thyroxine assay system can be efficiently and reproducibly effected by a manner whereby the non-specific binding in the system is monitored at a low constant level if the bound fraction is precipitated with an aqueous sulfate salt solution to which a minor but effective amount of added animal serum has been previously added.

DETAILED DESCRIPTION OF THE INVENTION

The assay of the subject invention was developed in an effort to provide a "single tube" thyroid hormone assay which would not utilize blocking agents nor an external solid phase sorption step and require a minimum of manipulation by the laboratory technician.

First, I have discovered that endogenous thyroid hormone binding protein can be initially inactivated and thereby separated from endogenous thyroid hormone by acid treatment, and thereafter the pH of the resulting mixture can be raised and thyroid hormone antibodies added thereto to competitively bind with the endogenous thyroid hormone without interference from the endogenous protein. This is quite surprising in view of the fact that acid inactivated thyroid hormone binding protein is known to renature at higher pH's and interfere with competitive binding between thyroid hormone and exogenous thyroid hormone binding protein by actually entering into the competitive binding reaction. Thus, I have found that a radioimmunoassay for thyroid hormone can be carried out immediately after acid separation of endogenous thyroid hormone from endogenous thyroid hormone binding protein after a single upward pH adjustment of the mixture and without first having to remove the endogenous thyroid hormone binding protein from the mixture.

Secondly, as stated above, most sorbents are dependent upon the total protein concentration in the mixture such that slight variations in the protein concentration of the samples can affect the percentage uptake of the sorbent. In addition, an effective thyroxine radioimmunoassay must have a low reproducible non-specific binding of the thyroid hormone which in essence is a low but uniform degree of binding of the thyroid hormone to constituents other than the antibody.

The thyroid hormone radioimmunoassay of the subject invention utilizes a salt precipitation step to separate the bound hormone from the free hormone in solution. Carrier or adjuvant proteins are conventionally added to such mixtures before the addition of sulfate in order to effect and expedite precipitation. However, I have found that the adjuvant protein can be mixed with the sulfate prior to introduction to the assay mixture. Using this combination as a precipitant, I have found that a constant, reproducible non-specific binding as well as an acceptable spread between the hypothyroid and hyperthyroid samples will result. Furthermore, the use of this combination as precipitant permits the use of a wide range of volumes of the serum sample, and allows the assay of serum samples containing a wide range of protein concentration.

The subject invention will be described in detail in relation to radioimmunoassay for thyroxine, even though one have ordinary skill in the art can esaily adapt my novel procedure to assay triiodothyronine and other thyronines.

Before the endogenous serum thyroxine can be assayed utilizing the improved salt precipitation step of the subject invention, the hormone must be efficiently and reproducibly extracted from a serum sample. In addition, all endogenous protein which could possibly bind thyroxine during the several steps of the assay must be completely inactivated. In accordance with one embodiment of the subject invention, the endogenous thyroxine is extracted from the serum sample with an acid solution. The acid solution is generally maintained at a pH within the range of from about 1.0 to 2.2. The preferable pH range is from about 1.0 to about 2.0. Any stable acid solution which is nondeleterious to the thyroid hormone can be used in the scope of the subject invention. For example, aqueous solutions of HCl, $H_2SO_4$, $H_3PO_4$ and the like can be used within the scope of the subject invention. HCl is the preferred acid. These materials can be buffered with suitable buffering agents, e.g., salts of weak acids at a concentration of about 0.02 to 0.07 M. Also, the ionic strength of the acid solution can be maintained by the presence of suitable materials such as neutral salts, e.g., NaCl, KCl and the like at a concentration of 0.02 to 0.07 molar.

In general, at least about 10 and preferably about 20 volumes of the acid extraction reagent is combined with each volume of the serum sample. The pH of the resulting mixture should be in the range of from about 1.3 to about 3.0. Complete inactivation of the endogenous thyroxine binding proteins is accomplished immediately, even though the inactive proteins remain in solution. For example, the serum is added to the acid extraction solution contained within a vial, and the vial is shaken for a few seconds (generally 10 to 15 seconds) to admix thoroughly the serum and the acid extraction solution. This will allow time for the acid solution to break the bonds between the thyroxine and the thyroxine binding protein and to inactivate completely the thyroxine binding protein.

Now that the resulting solution contains all of the endogenous thyroxine therewithin, and substantially all of the thyroxine binding protein has been deactivated, it is necessary to adjust the pH of the solution upwardly to a suitable pH in which competitive binding of the thyroid hormone and thyroid antibody can take place while adding to the solution a tracer quantity of radioactively labelled thyroid hormone (T-4) and a known quantity of antiserum containing the thyroid hormone antibodies. In accordance with a preferred embodiment of this invention, the radioactive thyroid hormone followed by the antiserum is added to the acid solution containing the unknown quantity of endogenous thyroid hormone. More specifically, the solution containing the radioactive thyroxine can comprise a solution having a pH within the range of about 7.6 to 9.0 and preferably about 8.3, and will contain a tracer quantity of radioactively labelled thyroid hormone, and preferably a buffer to maintain the pH of the solution. A suitable such solution comprises 0.04 M sodium barbital carrier which is adjusted to a pH of 8.3 by the addition of hydrochloric acid which contains the tracer quantity of T-4 $^{125}I$.

Any radioactive isotope of iodine, tritium, or carbon can be used. It is preferred that a hormone be utilized which is labelled with $^{125}I$. The buffered solution containing the tracer quantity of radioactively labelled thyroid hormone thyroxine, which is at least 20 and preferably about 40 volumes greater than the serum sample, is added to the acid solution and the contents are thereafter thoroughly mixed by shaking.

Next a solution containing the antithyroxine serum is added to the resulting solution. The antiserum can contain a suitable buffer such as sodium barbital and can generally have a pH within the range from about 7.6 to 9.0. The volume of the antiserum solution added to the test mixture can be the same as that used to deliver the radioactive isotope labelled thyroid hormone to the test mixture. After the thyroxine antiserum solution has been added to the solution containing the extracted thyroid hormone and the radioactive quantity of thyroid hormone, the resulting mixture is thoroughly mixed. The resulting solution will have a pH in the range of from about 7.0 to 8.5 and preferably about 7.4–8.4 and is incubated at room temperature from 30 to about 60 minutes to allow the formation of the thyroxine-antibody complexes. Since the antibody will bind both the radioactive thyroxine and serum thyroxine equally well, the amount of radioactive thyroxine recovered will reflect the concentration of thyroxine in the original sample. As is well known, the antiserum used in this step should have a high specificity for thyroxine. Furthermore, as previously noted, the inactivated thyroid hormone binding protein in the mixture surprisingly does not interfere with the competitive binding between the thyroid hormone and the antibody.

Once the solution is equilibrated such that the competitive binding between the thyroxine antibodies and thyroxine is complete, the antibodies containing bound hormone are precipitated in accordance with the improved salt precipitation step of the subject invention. The precipitant solution which is used in the scope of the subject invention comprises an aqueous solution of a water soluble sulfate salt which will effectively precipitate proteinaceous materials without deleteriously precipitating free hormone from solution. Examples of suitable sulfate salts which can be used are the alkali metal sulfates such as sodium and potassium sulfate, ammonium sulfate, and zinc sulfate. Because of the solubility range, availability and convenience, the most preferred salt is ammonium sulfate. The concentration of the ammonium sulfate can vary according to the amount of aqueous precipitant fluid which is desired to be used. Generally, the concentration in the precipitant solution should be such that when it is admixed with the thyroxine-antibody containing solution, the resulting concentration of sulfate will be in the range of about 20 to 30% by weight and preferably in the range of about 23 to 27% by weight and most preferably about 23 to 24% by weight. I have found that the concentration of the sulfate in the precipitant solution can conveniently range from about 30 to about 40% by weight and preferably from about 33 to 39% by weight thereof.

In addition to the sulfate, I have found it necessary to add a minor but effective amount of animal serum as adjuvant to the antibody-thyroxine containing solution at the time of precipitation in order to obtain a low but reproducible order of non-specific binding and a marked distinction in thyroxine levels of hypothyroid and hyperthyroid serum samples. Furthermore, the use of the above combination permits the use of a wide range of sample volume (i.e., from about 2 to about 50 microliters), and allows the assay of serum samples containing a wide range of protein concentration. In general, the amount of added serum which is necessary to accomplish this result is a volume greater than the initial volume of the serum sample being tested. Generally, any type of animal serum can be utilized as an adjuvant in this manner even though I have found some variation in the quantity of serum which must be used which is directly related to the specie of animal from which the serum is obtained. In general, when utilizing a serum sample of 10 microliters or less and when using bovine serum, sheep serum or human serum as the source of adjuvant protein, the volume of this added carrier protein must be greater than about 4 times the initial volume of the serum sample being tested and preferably it is greater than about 6 times the volume of the sample being tested and can be a much larger volume, e.g., from 12 to 20 times the volume of the initial sample. In essence, once the total protein in the solution reaches about 60 microliters then a constant non-specific binding and an acceptable percent spread is obtained and further amounts of protein added either from the sample or otherwise will not deleteriously effect the analyses. I have found that approximately twice as much rabbit serum is needed than the above bovine, sheep or human serum and about one-half as much horse serum is needed than the bovine, sheep or human serum. The serum is preferably contained within the concentrated sulfate precipitant solution which as stated above generally has a concentration of about 30 to 40% by weight and preferably of about 33 to 39% by weight.

To separate the free from the bound fractions in the test solution, a sufficient quantity of the precipitant solution is added to the sample solution containing the thyroxine and antibody to result in a final concentration of the sulfate between about 20 and 30 weight percent thereof as set forth above and to result in a sufficient concentration of the adjuvant carrier protein within the ranges as set forth above. The mixture should be thoroughly admixed, for example, by covering the tube in which it is contained and inverting it from 5 to 20 times. The precipitate of the antibody containing the bound hormone together with the adjuvant proteins forms immediately at the lower sulfate concentration and the resulting mixture should be centrifuged until the precipitated proteinaceous material forms a small button within the bottom of the vessel.

Thereafter, either the free fraction in the supernatant fluid or bound fraction in the precipitate should be counted in a scintillation well counter. It is preferred to count the bound fraction. The reading of the scintillation counter is compared to the total number of counts contained in the amount of tracer radioisotopically labelled thyroid hormone which was initially added. The percent antibody bound values are thus obtained. The percent antibody bound values are then correlated with standard values obtained by measuring percent antibody bound of standard samples containing known amounts of thyroid hormone to thereby determine the amount of thyroid hormone within the sample in a manner well known in the art.

The minor but effective amount of adjuvant serum protein is necessary in order to provide an assay which can utilize various volumes of serum and which has constant non-specific binding and also has an acceptable recovery range between high and low thyroxine values. It is believed that the principle active ingredient within the serum which effects the desired but unexpected results is gamma globulin. Generally, most animal serum contains between about 0.5 and 2 grams gamma globulin per 100 milliliters serum while the total protein in the serum is about 5 to 8 grams per 100 milliliters serum. It is noted at this point, while it is believed that gamma globulin is the active ingredient in the serum for this purpose, because of convenience and availability, it is preferred to utilize the entire serum sample. In general, when utilizing bovine, human or sheep serum in quantities of 4 times the volume of the initial serum sample or less, fluctuating, non-reproducible values of non-specific binding have been determined in addition to an unacceptable percent spread between the high and low thyroxine containing serum samples. However, when using such serum in volumes greater than about 4 times the initial volume of the serum, a plateau is reached where substantially constant non-specific binding is obtained and an excellent spread in recovery values is also obtained. This plateau is well defined at about 6 volumes greater than the volume of the initial sample and continues with no variation with added quantities of protein up to 12 volumes and more based upon original volume of the sample serum.

The following examples are given to better facilitate the understanding of this invention and to show some specific preferred embodiments of the subject invention and are therefore not intended to limit the scope of the claimed invention.

EXAMPLE I

This example illustrates the assay reproducibility of the novel thyroxine assay of the subjecting invention. The specific assay comprised the use of the following reactant solutions:

a. The extractant solution consisted of a solution containing 0.025 N HCl; and 0.05 N KCl;
b. The T-4 $^{125}$I reagent solution contained a tracer quantity of radioisotope T-4 $^{125}$I in a 0.04 molar sodium barbital solution which contained sufficient HCl to render a pH thereof of 8.3;
c. The T-4 antiserum contained thyroxine antibodies (formed in a rabbit) and contained within 0.04 M sodium barbital solution which had been adjusted with HCl to render a final pH of 8.3;
d. The precipitant solution consisted of an aqueous solution containing 37% by weight ammonium sulfate and containing bovine serum at a concentration of 4 volumes percent;
e. The standards utilized in running the test were as follows:
    1 microgram thyroxine per deciliter
    6 micrograms thyroxine per deciliter
    12 micrograms thyroxine per deciliter
    18 micrograms thyroxine per deciliter The above solutions were utilized to assay frozen pools of hypothyroid serum, normal serum and hyperthyroid serum by 11 different technicians.

The test procedure utilized included initially adding 10 microliters of a serum sample (or standard as the case may be) to 200 microliters of the extraction solution. After this step, the resulting solution was thoroughly admixed, and then 400 microliters of the T-4 - $^{125}$I reagent were added to the resulting solution and the solution agitated. After this, 400 microliters of the T-4 antiserum solution were added and the resulting solution thoroughly admixed. At this point, the solution was incubated at room temperature for 45 or 60 minutes, and at the end of the incubation period, the precipitate in the sulfate solution was resuspended and 2 milliliters of this suspension were added to each tube containing the test solution. This resulted in 80 microliters of adjuvant serum being added to each original 10 microliter sample and a final sulfate concentration in each test solution of 23.7% by weight. The tubes were capped and each tube inverted gently about 10 times.

Then within 20 minutes after the addition of the precipitant, the tubes were centrifuged for 10 minutes at 1000–1500 gravities or 2000–2500 rpm and within 3 hours the supernatant was discarded and the resultant button of precipitant counted in a scintillation well counter. The results of the runs are set forth in Table 1 below:

Table 1

| Serum Pool | Hypo-thyroid | Normal | Hyper-thyroid |
|---|---|---|---|
| Number of Observations | 212 | 317 | 210 |
| Number of Days | 16 | 15 | 16 |
| Number of Lots | 2 | 2 | 2 |
| Number of Technicians | 12 | 11 | 12 |
| Mean ($\mu g/dl$) | 3.2 | 7.9 | 14.1 |
| Standard Deviation ($\mu g/dl$) | 0.28 | 0.30 | 0.47 |
| Coefficient of Variation (%) | 8.8 | 3.8 | 3.3 |

As shown from the table, the reproducibility of the assay is excellent.

EXAMPLE II

The linearity of the radioimmunoassay of the subject invention is demonstrated in this example utilizing the assay solutions described in Example I above. Specifically, the endogenous thyroxine from 3 serum pools was initially measured using the procedure set forth in Example I above. Thereafter, quantities of 5, 10, 15 and 20 micrograms per deciliter of crystalline thyroxine were added to 4 samples, respectively, from each of the 3 serum pools and the resulting samples were assayed in accordance with the procedure set forth in Example I to illustrate the uniformity of the percent recovery obtained from running the test. The results are set forth in Table 2 below:

Table 2

| Serum Pool | Measured Endogenous T4 ($\mu g/dl$) | Added Exogenous T4 ($\mu g/dl$) | Predicted Total T4 ($\mu g/dl$) | Measured Total T4 ($\mu g/dl$) | Recovered Exogenous T4 ($\mu g/dl$) | Recovered Exogenous Percent |
|---|---|---|---|---|---|---|
| 1 | 3.3 | 5 | 8.3 | 8.3 | 5.0 | 100 |
|  |  | 10 | 13.3 | 13.4 | 10.1 | 101 |
|  |  | 15 | 18.3 | 18.4 | 15.1 | 101 |
|  |  | 20 | 23.3 | 23.6 | 20.3 | 102 |
| 2 | 3.6 | 5 | 8.6 | 8.7 | 5.1 | 102 |
|  |  | 10 | 13.6 | 13.5 | 9.9 | 99 |
|  |  | 15 | 18.6 | 18.8 | 15.2 | 101 |
|  |  | 20 | 23.6 | 24.0 | 20.4 | 102 |
| 3 | 3.0 | 5 | 8.0 | 7.9 | 4.9 | 98 |
|  |  | 10 | 13.0 | 12.9 | 9.9 | 99 |
|  |  | 15 | 18.0 | 18.1 | 15.1 | 101 |
|  |  | 20 | 23.0 | 23.0 | 20.0 | 100 |

The above results illustrate excellent recovery of the added T-4 and linearity of the test system.

EXAMPLE III

This example is presented to illustrate the constant reproducible plateau of non-specific binding of the hormone to the antibody which is reached when the precipitant solution contains bovine serum in excess of 4 volumes per volume of the initial serum sample. In each instance, a solution containing a known quantity of thyroid hormone (a 10 microliter sample), a tracer quantity of radioactively labelled thyroid hormone, and a known quantity of antiserum were contacted with different precipitated solutions. Furthermore, the non-specific binding for each precipitant solution was determined by running each test but with the antiserum eliminated from the buffered antiserum solution. The precipitant solution was varied both in concentration of the ammonium sulfate and the carrier protein as illustrated in the table below and the non-specific binding of three different serum standards were tested by eliminating the antiserum from the antiserum buffer solution as described in Example III. The results are set forth in Table 4.

Table 4

| | Concentration of $(NH_4)_2SO_4$ In Precipitant Solution | | | | | | | | | | | | | | |
|---|---|---|---|---|---|---|---|---|---|---|---|---|---|---|---|
| | 34% Carrier Protein Volume | | | 35% Carrier Protein Volume | | | 36% Carrier Protein Volume | | | 37% Carrier Protein Volume | | | 38% Carrier Protein Volume | | |
| Non-specific Binding | 40$\mu$l | 80$\mu$l | 120$\mu$l | 60$\mu$l | 80$\mu$l | 100$\mu$l | 60$\mu$l | 80$\mu$l | 100$\mu$l | 60$\mu$l | 80$\mu$l | 100$\mu$l | 40$\mu$l | 80$\mu$l | 120$\mu$l |
| Serum Stds |  |  |  |  |  |  |  |  |  |  |  |  |  |  |  |
| 0.5 $\mu$g% | 5.2 | 4.6 | 4.5 | 5.9 | 5.5 | 5.3 | 6.1 | 5.7 | 5.6 | 6.7 | 6.6 | 6.8 | 8.0 | 7.6 | 7.5 |
| 18 $\mu$g% | 5.2 | 4.5 | 4.5 | 5.7 | 5.6 | 5.4 | 6.1 | 5.6 | 5.6 | 6.9 | 6.8 | 6.8 | 8.6 | 7.7 | 7.4 |
| Normal Human Serum | 4.9 | 4.5 | 4.6 | 5.6 | 5.4 | 5.4 | 5.8 | 5.5 | 5.5 | 6.9 | 6.8 | 6.7 | 8.1 | 7.4 | 7.2 |
| Average | 5.1 | 4.5 | 4.5 | 5.7 | 5.5 | 5.4 | 6.0 | 5.6 | 5.6 | 6.9 | 6.7 | 6.8 | 8.2 | 7.4 | 7.4 |

EXAMPLE IV

This example indicates the constant degree of non-specific binding and excellent spread of recovery values between hypothyroid and hyperthyroid serum samples when utilizing the test of the subject invention with the precipitant fluid containing the minor but effective quantity of added serum as adjuvant. More specifically, the procedure set forth in Example III was utilized to assay various serum standards except that the concentration of the serum in the precipitant solution was varied such that the resultant test solution would carry 60, 70, 80, 90, 100 and 110 microliters of added serum which is added with the precipitant to contact the test solution containing the initial 10 microliters of the serum sample. As will be noted when the carrier protein is present in the precipitant solution in quantities of 6 times the volume of initial sample or more, the value of the non-specific binding stabilizes; whereas when the quantity of the carrier protein is only 4 times that of the initial volume of the sample, the non-specific binding varies in an unpredictable manner. The results are set forth in Table 5 below:

Table 5

| Sample Concentration (μg/dl) | Precipitant with 60μl serum | | | Precipitant with 70μl serum | | | Precipitant with 80μl serum | | | Precipitant with 90μl serum | | | Precipitant with 100μl serum | | | Precipitant with 110μl serum | | |
|---|---|---|---|---|---|---|---|---|---|---|---|---|---|---|---|---|---|---|
| | Non-Spec. Bind. | % Bound | Δ* | Non-Spec. Bind. | % Bound | Δ | Non-Spec. Bind. | % Bound | Δ | Non-Spec. Bind. | % Bound | Δ | Non-Spec. Bind. | % Bound | Δ | Non-Spec. Bind. | % Bound | Δ |
| 0.4 | 6.6 | 61.8 | | 6.6 | 61.1 | | 6.6 | 61.6 | | 6.6 | 59.1 | | 6.8 | 60.2 | | 6.4 | 60.5 | |
| | | 61.2 | | | 61.2 | | | 61.6 | | | 59.8 | | | 60.3 | | | 61.0 | |
| | | 61.2 | | | 61.0 | | | 60.8 | | | 59.7 | | | 59.6 | | | 60.6 | |
| | | (61.4)** | | | (61.1) | | | (61.3) | | | (59.5) | | | (60.0) | | | (60.7) | |
| 3.2 | | 48.2 | | | 48.9 | | | 48.6 | | | 47.6 | | | 46.6 | | | 47.4 | |
| | | 48.0 | | | 48.6 | | | 48.8 | | | 47.0 | | | 47.1 | | | 47.3 | |
| | | 48.8 | | | 48.2 | | | 48.5 | | | 47.0 | | | 47.2 | | | 47.7 | |
| | | (48.3) | 13.1 | | (48.6) | 12.5 | | (48.6) | 12.7 | | (47.2) | 12.3 | | (47.0) | 13.0 | | (47.5) | 13.2 |
| 6.0 | 6.8 | 40.2 | | 6.7 | 39.9 | | 6.6 | 40.2 | | 6.6 | 39.0 | | 6.7 | 39.0 | | 6.5 | 39.1 |
| | | 40.2 | | | 40.2 | | | 40.2 | | | 38.8 | | | 39.2 | | | 39.2 | |
| | | 39.8 | | | 39.7 | | | 40.5 | | | 38.8 | | | 38.8 | | | 38.8 | |
| | | (40.1) | 8.2 | | (39.9) | 8.7 | | (40.3) | 8.3 | | (38.9) | 8.3 | | (39.0) | 8.0 | | (39.0) | 8.5 |
| 12.0 | | 28.8 | | | 29.0 | | | 28.9 | | | 28.0 | | | 28.5 | | | 28.5 | |
| | | 29.3 | | | 29.0 | | | 29.0 | | | 27.9 | | | 28.8 | | | 28.3 | |
| | | 29.0 | | | 29.0 | | | 28.9 | | | 28.1 | | | 28.3 | | | 28.7 | |
| | | (29.0) | 11.1 | | (29.0) | 10.9 | | (28.9) | 10.9 | | (28.0) | 10.9 | | (28.5) | 10.5 | | (28.5) | 10.5 |
| 18.0 | 6.7 | 24.0 | | 6.6 | 23.7 | | 6.6 | 23.7 | | 6.3 | 22.8 | | 6.3 | 23.1 | | 6.4 | 23.3 |
| | | 23.7 | | | 23.8 | | | 23.8 | | | 23.2 | | | 23.3 | | | 23.4 | |
| | | 23.6 | | | 23.7 | | | 23.6 | | | 22.8 | | | 23.1 | | | 23.4 | |
| | | (23.8) | | | (23.7) | | | (23.7) | | | (22.9) | | | (23.2) | | | (23.4) | |
| TOTAL | | | 5.2 | | | 5.3 | | | 5.2 | | | 5.1 | | | 5.3 | | | 5.1 |
| | | | 37.6 | | | 37.4 | | | 37.6 | | | 36.6 | | | 36.8 | | | 37.3 |

*Represents the differences in % Bound between samples
**Numbers in parentheses are averages

EXAMPLE V

This example is presented to illustrate the specificity and sample serum protein independence of the radioimmunoassay of the subject invention. Specifically, the endogenous thyroxine of different sample volumes of various sera containing elevated and decreased protein levels was measured using the test procedure and the reactant solutions described in Example I. The results are set forth in Table 6 below:

Table 6

| Type of Serum Sample | Serum Volume ($\mu$l) | Measured T4 ($\mu$g/dl) | Corrected* to 10$\mu$l ($\mu$g/dl) |
|---|---|---|---|
| Hyperthyroid | 10 | 17.9 | 17.9 |
| Total Protein, 7.3 g/dl | 7.5 | 13.7 | 18.3 |
|  | 5.0 | 9.4 | 18.8 |
|  | 2.5 | 4.7 | 18.8 |
|  | 1.67 | 2.9 | 17.4 |
| Hyperthyroid, | 10 | 13.7 | 13.7 |
| Total Protein, 7.5 g/dl | 7.5 | 10.6 | 14.1 |
|  | 5.0 | 7.4 | 14.8 |
|  | 2.5 | 3.5 | 14.0 |
|  | 1.67 | 2.2 | 13.2 |
| Alpha Globulins, 2.1 g/dl | 10 | 15.4 | 15.4 |
| (Elevated) | 7.5 | 11.5 | 15.3 |
|  | 5.0 | 7.9 | 15.8 |
|  | 2.5 | 4.1 | 16.4 |
| Albumin, 5.4 g/dl (Elevated) | 10 | 7.7 | 7.7 |
|  | 5.0 | 4.0 | 8.0 |
|  | 3.3 | 2.5 | 7.5 |
|  | 2.5 | 1.8 | 7.2 |
| Gamma Globulins, 4.6 g/dl | 10 | 7.3 | 7.3 |
| (Elevated) | 5.0 | 3.6 | 7.2 |
|  | 3.3 | 2.5 | 7.5 |
|  | 2.5 | 1.7 | 6.8 |
| Hypothyroid | 10 | 2.5 | 2.5 |
| Total Protein, 8.2 g/dl | 20 | 5.3 | 2.7 |
|  | 30 | 8.2 | 2.7 |
| Total Protein, 4.5 g/dl | 10 | 3.1 | 3.1 |
| (Decreased) | 20 | 6.7 | 3.4 |
|  | 30 | 10.4 | 3.5 |
| Albumin, 0.9 g/dl | 10 | 3.5 | 3.5 |
| (Decreased) | 20 | 7.2 | 3.6 |
|  | 30 | 10.4 | 3.5 |
| Feline (10 Animals - | 10 | 1.3 | 1.3 |
| 3 Determinations Each) | 20 | 3.6 | 1.6 |
|  | 30 | 5.4 | 1.8 |
| Canine (10 Animals - | 10 | 1.4 | 1.4 |
| 3 Determinations Each) | 20 | 3.0 | 1.5 |
|  | 30 | 4.8 | 1.6 |
| Equine (10 Animals - | 10 | 0.8 | 0.8 |
| 3 Determinations Each) | 20 | 2.2 | 1.1 |
|  | 30 | 3.8 | 1.3 |

*These values are corrected only to the volume of 10$\mu$l and do not reflect a correction for non-specific binding. All values for any serum would be equal if corrected for non-specific binding.

While this invention has been described in relation to its preferred embodiments, it is to be understood that various modifications thereof will be apparent to those skilled in the art upon reading this specification, and it is intended to cover such modifications as fall within the scope of the appended claims.

I claim:

1. A method of measuring the level of thyroid hormone in a sample of serum containing endogenous thyroid hormone and endogenous thyroid hormone binding protein comprising:
   a. admixing said serum sample with an effective amount of an aqueous acid solution sufficient to separate said thyroid hormone from said thyroid hormone binding protein;
   b. adjusting the pH of the resulting mixture to a value in the range of from about 7.0 to about 8.5 in the absence of blocking agents while adding thereto a known amount of radioactively labeled thyroid hormone and a known amount of thyroid hormone binding antibodies and allowing the resulting solution to equilibrate;
   c. thoroughly admixing the resulting equilibrated mixture from step (b) with an aqueous solution of a water soluble sulfate which contains sufficient sulfate such that the resulting mixture has a sulfate concentration between about 20 and 30 weight percent to thereby result in precipitation of said thyroid hormone binding protein material containing thyroid hormone bound thereto and leave free thyroid hormone in the solution;
   d. separating the precipitated material from said solution; and
   e. counting with a scintillation counter one of (1) the free radioactively labeled thyroid hormone in said resulting solution, and (2) the bound radioactively labeled thyroid hormone bound to said thyroid hormone binding antibodies in said precipitate.

2. The method of claim 1 wherein said aqueous acid solution is an aqueous solution of HCl having a pH in the range of about 1.0 to about 3.0.

3. The method of claim 1 further comprising an effective amount of animal serum admixed with said aqueous solution of said water soluble sulfate.

4. The method of claim 3 wherein said animal serum is selected from bovine, human and sheep serum.

5. The method of claim 4 wherein the volume of said animal serum added to said mixture is at least 6 times larger than the volume of said serum sample and said volume of said serum sample is up to about 10 microliters.

6. The method of claim 5 wherein the volumetric ratio of said serum sample to said animal serum added thereto is in the range of from about 1:6 to about 1:20.

7. The method of claim 6 wherein said volumetric ratio is in the range of from about 1:6 to about 1:12.

8. The method of claim 6 wherein said animal serum is bovine serum.

9. The method of claim 6 wherein said animal serum is horse serum.

10. The method of claim 9 wherein said volume of said horse serum added to said serum sample is at least twice as large as said serum sample.

11. The method of claim 6 wherein said animal serum is rabbit serum.

12. The method of claim 11 wherein said volume of said rabbit serum added to said sample is 8 times as large as the volume of said sample serum.

13. The method of claim 1 wherein said sulfate solution is an aqueous solution of a sulfate selected from alkali metal sulfates and ammonium sulfates.

14. The method of claim 13 wherein said aqueous sulfate solution is an aqueous solution of ammonium sulfate having a concentration in the range from about 30 to about 40 weight percent ammonium sulfate.

15. The method of claim 14 wherein said resulting mixture has a sulfate concentration in the range of from about 23 to 27% by weight thereof.

16. The method of claim 15 wherein said thyroid hormone is thyroxine.

17. The method of claim 15 wherein said thyroid hormone is triiodothyronine.

18. In a radioimmunoassay for thyroid hormone in a serum sample having a known volume and containing an unknown quantity of thyroid hormone and thyroid hormone binding protein wherein said thyroid hormone is initially separated from said thyroid hormone binding protein and thereafter known quantity of radioactively labeled thyroid hormone and a known quantity of thyroid hormone antibodies are added thereto and allowed to competitively bind, and thereafter, free thyroid hormone (not bound to thyroid hormone antibody) is separated from thyroid hormone bound to thyroid hormone antibody, and the amount of said unknown hormone is determined by counting with a scintillation counter one of (a) said radioactively labelled hormone bound to said thyroid hormone antibody, and (b) said radioactively labeled thyroid hormone which is not bound to said thyroid hormone antibody, the improvement comprising:

initially separating said thyroid hormone from said thyroid hormone binding protein contained in said serum sample by contacting said serum sample with an acidic solution, and thereafter adjusting the pH of said mixture to a higher value in the absence of a blocking agent and adding said known quantity of said radioactively labeled thyroid and said known quantity of said thyroid hormone antibodies thereto without first removing said thyroid hormone binding protein from said mixture.

19. The method of claim 18 wherein said acidic solution is an aqueous solution of HCl having a pH of from about 1 to about 3.

20. The method of claim 19 wherein said aqueous solution has a pH in the range of from about 1 to about 2.0.

* * * * *